US00PP10770P

United States Patent [19]

Hartenhof

[11] Patent Number: Plant 10,770

[45] Date of Patent: Feb. 2, 1999

[54] MCINTOSH APPLE TREE NAMED 'HARTENMAC NS 219'

[75] Inventor: Jacob A. Hartenhof, Nova Scotia, Canada

[73] Assignee: Adams County Nursery, Inc., Aspers, Pa.

[21] Appl. No.: 802,035

[22] Filed: Feb. 18, 1997

[51] Int. Cl.[6] ..... A01H 5/00

[52] U.S. Cl. ..... Plt./34.1

[58] Field of Search ..... Plt./34.1

*Primary Examiner*—Elizabeth Kemmerer

*Attorney, Agent, or Firm*—Driggs, Isabella, & Lucas Co., L.P.A.

[57] ABSTRACT

An apple tree of the McIntosh variety, producing an apple of the best quality having an excellent sweet, juicy taste with a pronounced aroma and firm, fine and crisp white flesh possessing a green tint. The color is a bright red blush with small, pale green yellow dots fairly uniform thereon. It has a few-branching, spur-habit and semi-dwarfing growth habit being somewhat smaller than standard McIntosh.

3 Drawing Sheets

BACKGROUND OF THE DISCLOSURE

This invention relates to apple trees and, more specifically, to those of the McIntosh variety. As will be understood by those skilled in the art, trees of this variety grown in this climate are hardy and produce a good keeping and tasting apple.

I discovered the tree of this application as a limb sport of the McIntosh variety in orchards under my control near Kentville, Nova Scotia, Canada. It was selected because of its compact spurry growth habit which is proven stable over repropagations and the superior fruit color, size, uniformity and storability along with the excellent sweet taste, qualities which are very distinctive and attractive from a commercial standpoint over other McIntosh.

I have caused the tree, which I name 'NS219', to be repoduced asexually by cuttings, at the Agriculture Canada Research Station in Kentville, Nova Scotia, Canada, and find that its characteristics are constant and stable through successive generations.

SUMMARY OF THE INVENTION

As will be understood from a condsideration of the drawings, the tree of this invention has some outstanding differences from known varieties. In particular, it produces an apple of the best quality having an excellent sweet, juicy taste with a pronounced aroma and firm, fine and crisp flesh possessing a green tint. The color is a bright red blush with small, pale green yellow dots fairly uniform thereon. The tree of this invention has fewer lateral branches and more spurs per linear foot than other standard McIntosh varieties except for the extreme compact 'Wijick'.

The tree is medium in size, approximately one-half the size of a standard McIntosh tree and about ⅔ the size of a commerical spur-type McIntosh tree.

Referring now to Table 1, the branch growth of the main shoots, lateral branches and spurs of the parent is compared with the corresponding branch growth of the main shoots, laterals and spurs of NS 219 is shown in the following table:

TABLE 1

| | Branch # | | 1 | 2 | 3 | 4 | avg | avg/yr |
|---|---|---|---|---|---|---|---|---|
| | | | McIntosh Parent | | | | | |
| 1995 | main shoot | cm | 16 | 27 | 11 | 33 | 21.7 | |
| 1996 | main shoot | cm | 35 | 44 | 35 | 34 | 37.0 | |
| 1997 | main shoot | cm | 26 | 58 | 27 | 23 | 33.5 | 30.7 |
| 1998 | terminals | # | 6 | 8 | 3 | 5 | 5.5 | |
| | | cm | 14 | 41 | 23 | 10.6 | 22.2 | |
| 1996 | laterals | # | 0 | 0 | 0 | 2 | 0.5 | |
| | | tot cm | 0 | 0 | 0 | 7.5 | 1.9 | |
| 1997 | laterals | # | 8 | 7 | 2 | 3 | 5.0 | |
| | | tot cm | 57 | 134 | 16.5 | 30 | 59.4 | |
| 1998 | laterals | # | 6 | 6 | 3 | 1 | 4.0 | 3.2 |
| | | tot cm | 34.5 | 54 | 14.5 | 7 | 20.1 | 27.1 |
| 1996 | spurs | # | 3 | 4 | 4 | 7 | 4.5 | |
| | | flowering | 0 | 0 | 0 | 0 | 0 | |
| 1997 | spurs | # | 9 | 11 | 9 | 14 | 10.8 | |
| | | flowering | 4 | 3 | 3 | 6 | 4.0 | |
| 1998 | spurs | # | 15 | 33 | 10 | 18 | 19.0 | 6.1 |
| | | flowering | 6 | 0 | 5 | 10 | 5.2 | 2.7 |
| | | fruitlets | 19 | 0 | 8 | 10 | 9.2 | |
| | | | NS 219 | | | | | |
| 1995 | main shoot | cm | 48 | 24 | 41 | 15 | 32.0 | |
| 1996 | main shoot | cm | 24 | 12 | 28 | 27 | 22.8 | |
| 1997 | main shoot | cm | 26 | 29 | 18 | 18 | 22.8 | 25.9 |
| 1998 | terminals | # | 1 | 1 | 1 | 5 | 2.0 | |
| | | cm | 6 | 0.5 | 8 | 23.5 | 9.5 | |
| 1996 | laterals | # | 0 | 0 | 0 | 3 | 0.8 | |
| | | tot cm | 0 | 0 | 0 | 26 | 6.5 | |
| 1997 | laterals | # | 0 | 0 | 0 | 3 | 0.8 | |
| | | tot cm | 0 | 0 | 0 | 29.5 | 7.4 | |
| 1998 | laterals | # | 3 | 0 | 2 | 5 | 2.8 | 1.5 |
| | | tot cm | 16 | 0 | 8 | 48.5 | 18.1 | 7.8 |
| 1996 | spurs | # | 19 | 11 | 15 | 7 | 13.0 | |
| | | flowering | 0 | 1 | 0 | 1 | 0.5 | |
| 1997 | spurs | # | 14 | 15 | 29 | 13 | 17.8 | |
| | | flowering | 10 | 11 | 9 | 1 | 7.8 | |
| 1998 | spurs | # | 27 | 20 | 37 | 47 | 32.8 | 21.2 |
| | | flowering | 29 | 4 | 25 | 35 | 23.2 | 10.5 |
| | | fruitlets | 14 | 2 | 33 | 34 | 20.8 | |

This information is summarized as follows:

TABLE 2

| | McIntosh Parent | 'NS219' |
|---|---|---|
| Main shoot avg/year cm | 30.7 | 25.9 |
| Laterals | | |
| avg/yr # | 3.2 | 1.5 |
| cm. | 27.1 | 7.8 |
| Total extension growth/yr. cm. | 57.8 | 33.7 |
| Spurs avg/yr # | 6.1 | 21.12 |
| Spurs/10 cm shoot # | 1.05 | 6.29 |
| Spurs flowering | | |
| avg/yr # | 2.7 | 10.5 |
| % | 44 | 49 |

The main shoots of the 'NS219' grew about 15% less (25.9 vs. 30.7) than those on the parent, the number of laterals was only about half (1.5 vs. 3.2) and total length of laterals was only about one quarter (7.8 cm vs. 27.1 ). Total extension growth for the three years of record was 33.7 cm with 'NS219' and 57.8 cm with the parent. Spur development was much stronger with 'NS219' with an average of 6.29 spurs per each 10 cm. of shoot as compared to only 1.05 spurs per 10 cm. of shoot for the parent clone. 'NS219' is significantly different from its parent McIntosh cultivar in that 'NS219' has less branching, less total shoot extension growth, and much more spur development along the shoots.

These properties of lateral branching and spur growth of six 'NS219' trees were also compared with the corresponding properties of five or six trees each of three other McIntosh cultivars, 'Summerland', 'Macspur' and 'Rogers'. These properties were measured on trees which were planted in the spring of 1993 with the measurements of top growth taken during a three year period between 1995 and 1998. Based on these measurements, the average shoot length of 'NS219' was substantially less than the shoot lengths of the other three McIntosh cultivars. Furthermore, the average number of spurs on the 'NS219' trees was considerably greater than on the other cultivars. The results are summarized in Table 3.

TABLE 3

| Cultivar | Shoot Length (cm) | Spur # (per 10 cm. of shoot) |
|---|---|---|
| 'NS219' | 98 | 3.2 |
| 'Summerland | 192 | 1.3 |
| 'Macspur' | 164 | 1.8 |
| 'Rogers' | 155 | 1.8 |

For purposes of this comparison, spurs are described as short shoots less than 2 cm. in length with more than three small leaves.

DESCRIPTION OF THE DRAWING

This new variety of apple tree is illustrated by the accompanying photographic drawings and depicts the plant by the best possible color representation using color photography.

BOTANICAL DESCRIPTION OF THE PLANT

Figure 1:
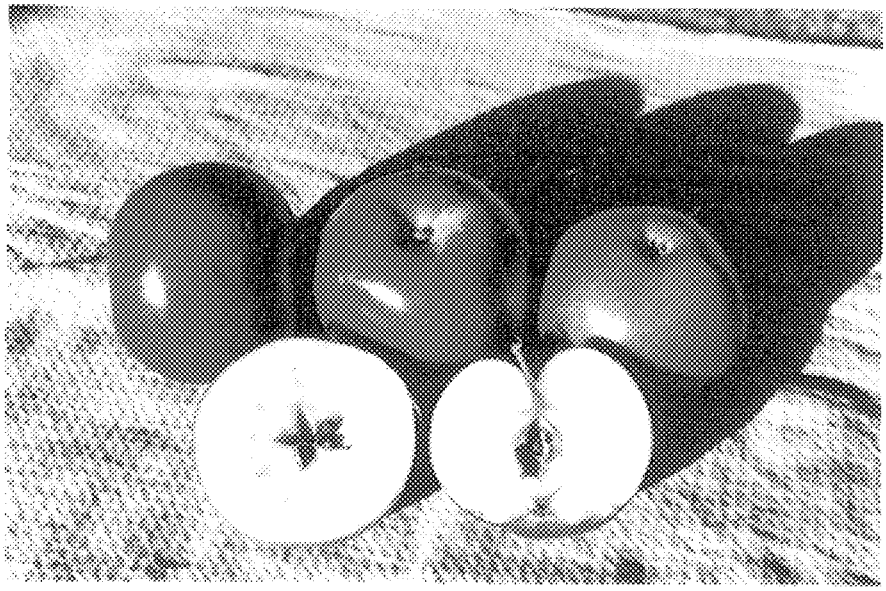
FIG. 1 is a close-up view showing fruit of the tree.
Figure 2:
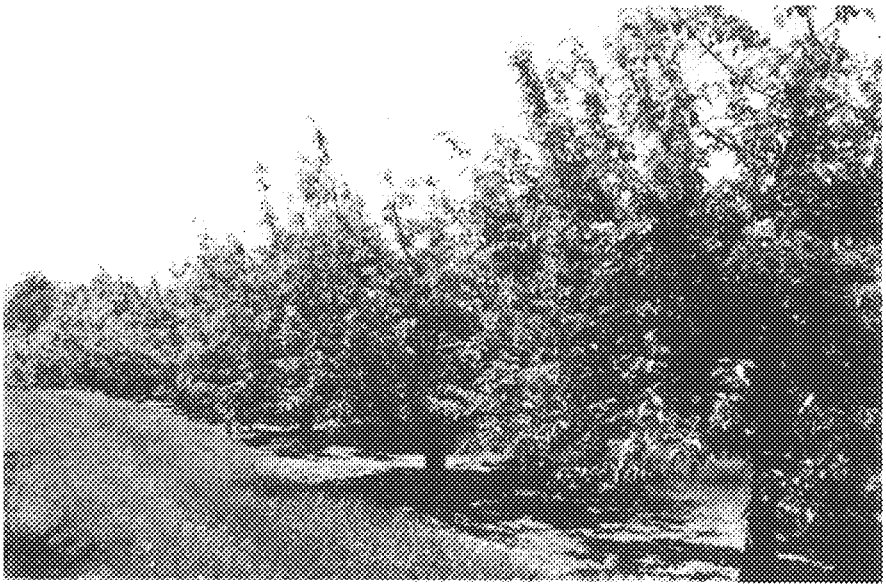
FIG. 2 is a photograph of the parent tree.
Figure 3:
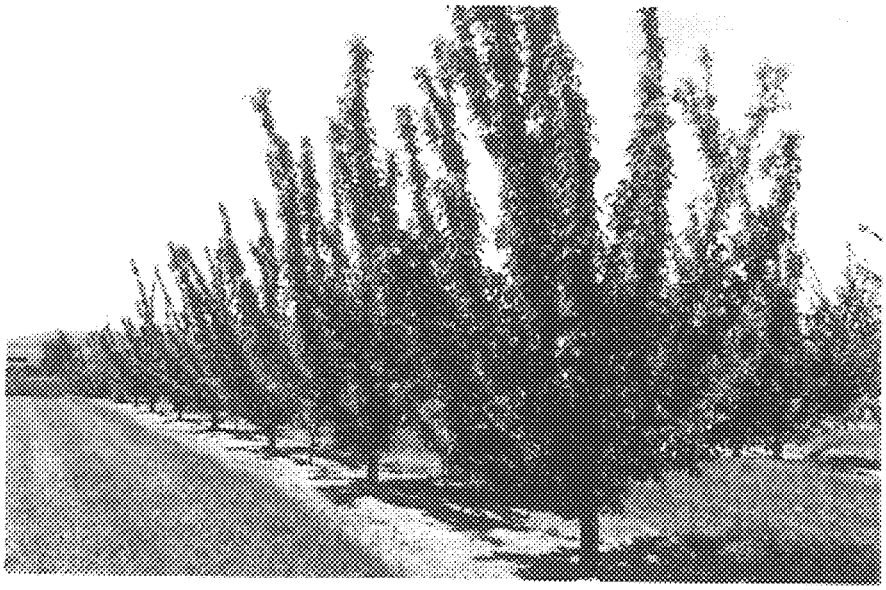
FIG. 3 is a photograph of the 'NS219' tree.

All color references below are measured against Munsell Color Cascade. Colors are approximate as color depends on horticultural practices such as light level and fertilization rate, among others.

Classification: *Malus domestica,* McIntosh Red.

Parentage: Sport of a 40 plus year old McIntosh apple tree.

Tree: Medium in size. Upright; medium height; average growth of main shoot 25.9 cm/year; limbs somewhat sparse, with many spurs; average of 6.29 spurs per 10 cm. of shoot. Open, medium growth habit, hardy, very productive, and regular bearer.

*Trunk.*—Medium and smooth.

*Branches.*—Thick to medium; smooth; little branching with about 1.5 lateral branches per year per main shoot; average growth of each lateral branch—7.8 cm/year and brown in color. Lenticels: Medium in number and medium in size.

*Leaves.13* Length—Blade 3½"; Width—2⅜". Medium in size; medium width; medium length; ovate; taper-pointed; medium thickness; medium green color, and smooth. Margin—Finely serrate. Petiole—1" in length; medium length, and medium thickness.

*Flowers.*—Medium size, white.

Fruit: Hardy at maturity.

*Size.*—Fairly uniform. Axial diameter—2½"; Transverse—2¾".

*Form.*—Fairly uniform to slightly variable; Fairly symmetrical to slightly asymmetrical. Fairly regular and globose to oblate in shape. Cavity—Symmetrical; abrupt at base; flaring toward apex; and acute. Depth ⅜"; Breadth 1 3/16". Markings—Non-existent to occasional slight russet. Basin—Symmetrical; abrupt; even; and glabrous.

*Stem.*—Medium to stout; slightly pubescent; and ½" in length.

*Calyx.—Closed. Segments—Persistent. Lanceolate; acute, and* ¼" in length. Separated at base, ascending, and connivent. Outer surface—Pubescent. Inner surface—Glabrous.

*Eye.*—Medium to small in size and partially closed.

*Skin.*—Medium thick, moderately tender, smooth, glossy, and waxed. Dots—Obscure and many. Small and even in size and circular. Color of dots—Pale greenish yellow. Fairly uniform distribution. Ground color—2.5GY 6/8. Color markings—Blushed and bright 2.5R 3/6. Bloom—Scant and wanting. General color effect—Bright red.

Flesh: Juicy. White with greenish tint color. Texture is firm, fine, and crisp. Flavor is subacid, sweet, and sprightly. Aroma is pronounced and excellent in quality.

Core: Median. Bundle area (longitudinal section) is medium to small, orbicular, and symmetrical. Halves of area are equal. Bundles are pale green in color with two whorls. Alternate bundle is distant from calyx and below stamens. Core lines are clasping. In cross-section—indistinct. Carpellary area is indistinct and medium in size. Calyx-tube is glabrous toward base and urn-shaped to funnel form. Stem of funnel is of medium length. Depth of tube to shoulder is ⅛" long. Entire depth is 5/16" in length. Styles—Present, united but distinct toward base, and pubescent throughout Stamens are in one distinct whorl and median. Axillary cavity is wanting. Seed cells are abaxile and open to closed. Cell walls are thin, tough, and ¾" in length. Breadth—½". Longitudinal section is orbicular and mucronate at apex. Entire surface is smooth and cross-section is broad.

Seeds:

*Number perfect.*—9.

*Imperfect.*—2.5.

*Largest number in one cell.*—2 (good).

*Length.*—5/16";

*Breadth*—3/16".

*Form.*—Obtuse.

*Color.*—Half cream and half brown.

Use:

*Market.*—Dessert.

Keeping quality: Good.

*Number of days in ordinary storage*—60. Longer in cold.

Resistance to:

*Insects.*—Medium.

*Diseases.*—Medium.

I claim:

1. A new and distinct apple tree as shown and described, characterized particularly as to novelty by its few-branching, spur-habit and semi-dwarfing habit of growth and its fruit having an attractive bright red blush coloration with small uniform green yellow dots and an excellent sweet, juicy taste with a pronounced aroma.

* * * * *